(12) United States Patent
Bender et al.

(10) Patent No.: US 11,883,158 B2
(45) Date of Patent: Jan. 30, 2024

(54) PREDICTING OCCUPANT EXIT FROM SUPPORT APPARATUS

(71) Applicant: Hill-Rom Services, Inc., Batesville, IN (US)

(72) Inventors: Justin Bender, Cincinnati, OH (US); Kin Meng Choi, Batesville, IN (US); Anthony Cohn, Harrison, OH (US); Frederick Keith Schultz, Bringhurst, IN (US); Sridhar Karimpuzha Seshadri, Blue Ash, OH (US); Thomas L. Simpson, Brookville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 249 days.

(21) Appl. No.: 17/322,031

(22) Filed: May 17, 2021

(65) Prior Publication Data

US 2021/0378551 A1    Dec. 9, 2021

Related U.S. Application Data

(60) Provisional application No. 63/035,196, filed on Jun. 5, 2020.

(51) Int. Cl.
*A61B 5/11* (2006.01)
*A61B 5/00* (2006.01)
*A61G 7/05* (2006.01)

(52) U.S. Cl.
CPC ........... *A61B 5/1115* (2013.01); *A61B 5/1126* (2013.01); *A61B 5/7264* (2013.01); *A61B 5/746* (2013.01); *A61B 5/747* (2013.01); *A61G 7/052* (2016.11); *A61G 7/0524* (2016.11); *A61G 2203/32* (2013.01); *A61G 2203/44* (2013.01)

(58) Field of Classification Search
None
See application file for complete search history.

(56) References Cited

U.S. PATENT DOCUMENTS

| 5,832,417 A | 11/1998 | Petrucelli et al. |
| 7,253,366 B2 | 8/2007 | Bhai |
| 8,919,211 B1 | 12/2014 | Hanson et al. |
| 9,579,047 B2 | 2/2017 | Clark et al. |
| 10,357,185 B2 | 7/2019 | Kostic et al. |

(Continued)

FOREIGN PATENT DOCUMENTS

| EP | 2508128 A1 | 10/2012 | |
| JP | 201379935 A | 5/2013 | |
| KR | 2008784 B1 * | 10/2019 | ............. A47C 31/12 |

OTHER PUBLICATIONS

KR2008784B1 Machine Translation (Year: 2019).*

(Continued)

*Primary Examiner* — Benjamin S Melhus
(74) *Attorney, Agent, or Firm* — Merchant & Gould P.C.

(57) ABSTRACT

An exit prediction system for a support apparatus receives data inputs from one or more force sensors without zeroing the one or more force sensors. Changes in the data inputs are detected to determine whether the detected changes indicate a movement trend. An exit prediction is determined based at least partially on the movement trend, and without combining the data inputs from the one or more force sensors to determine the occupant's weight. A notification is generated based on the exit prediction.

13 Claims, 8 Drawing Sheets

(56) References Cited

U.S. PATENT DOCUMENTS

| | | | |
|---|---|---|---|
| 10,376,214 B2 | 8/2019 | Hayes et al. | |
| 2006/0028350 A1* | 2/2006 | Bhai | A61B 5/1115 |
| | | | 177/144 |
| 2008/0129518 A1 | 6/2008 | Carlton-Foss | |
| 2008/0169931 A1* | 7/2008 | Gentry | A61B 5/1117 |
| | | | 600/300 |
| 2010/0045474 A1 | 2/2010 | Hayes et al. | |
| 2014/0267625 A1 | 9/2014 | Clark et al. | |
| 2015/0025327 A1* | 1/2015 | Young | A61B 5/024 |
| | | | 600/595 |
| 2016/0106345 A1* | 4/2016 | Kostic | A61B 5/1116 |
| | | | 5/652 |
| 2017/0156638 A1 | 6/2017 | Ribble et al. | |
| 2017/0224253 A1* | 8/2017 | Berlin | G08B 21/22 |
| 2017/0243459 A9 | 8/2017 | Sidhu et al. | |
| 2019/0266870 A1 | 8/2019 | Zhao et al. | |
| 2020/0155392 A1 | 5/2020 | Masuda | |
| 2021/0142643 A1* | 5/2021 | Susna | A61B 5/7264 |

OTHER PUBLICATIONS

European Search Report, Application No. EP 21 17 7596, dated Oct. 26, 2021, 9 pages.

"User Manual, VersaCare Bed from Hill-Rom, Product No. P3200 and P3201 (K model and newer)", 161956 Rev 2, 2011, 96 pages.

\* cited by examiner

(12) United States Patent

PREDICTING OCCUPANT EXIT FROM SUPPORT APPARATUS

BACKGROUND

A support apparatus, such as a hospital bed, can sometimes include systems used to predict an occupant exit. In some examples, an alarm is generated to notify a caregiver when an exit is predicted. Such systems are useful when an occupant is not authorized to exit a hospital bed without assistance, such as a patient diagnosed with Alzheimer's disease.

However, the systems that are used to predict occupant exit can sometimes fail to produce an alarm or can experience a delay in producing an alarm when an occupant is exiting the hospital bed. This can lead to negative patient outcomes. Also, bed exit systems can produce false alarms, which can place an undue burden on caregivers and lead to alarm fatigue.

SUMMARY

Generally, the present disclosure relates to predicting an exit from a support apparatus. In one example, the support apparatus is a hospital bed.

One aspect relates to an exit prediction system comprising: a processing unit; and a memory in communication with the processing unit; the memory storing machine-readable instructions that, when executed by the processing unit, cause the processing unit to: receive data inputs from one or more force sensors, the data inputs being received without zeroing the one or more force sensors; detect changes in the data inputs from the one or more force sensors; determine whether the detected changes indicate a movement trend; determine an exit prediction based at least partially on the movement trend, the exit prediction being determined without combining the data inputs from the one or more force sensors to determine the occupant's weight; and generate a notification based on the exit prediction.

Another aspect relates to a method of predicting an occupant exit from a support apparatus. The method comprises: receiving data inputs from one or more force sensors, the data inputs are received without zeroing the one or more force sensors; detecting changes in the data inputs from the one or more force sensors without combining the data inputs to determine an occupant's weight; determining whether the detected changes indicate a movement trend; determining an exit prediction based at least partially on the movement trend, the exit prediction indicating a likelihood for the occupant exit from the support apparatus; and generating a notification based on the exit prediction.

Another aspect relates to a method of automatically estimating a weight for an occupant positioned on a support apparatus without zeroing the support apparatus. The method comprises: receiving A/D counts from force sensors without zeroing the force sensors, the A/D counts being received from each force sensor individually; calculating a first moving average of the A/D counts from each force sensor; detecting a change in the A/D counts from at least one of the force sensors; determining whether an exit function is activated for the support apparatus; when the exit function is activated and the change in the A/D counts is detected, calculating a second moving average of the A/D counts from each force sensor; calculating a difference between the first and second moving averages of A/D counts; and converting the difference into an occupant weight.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
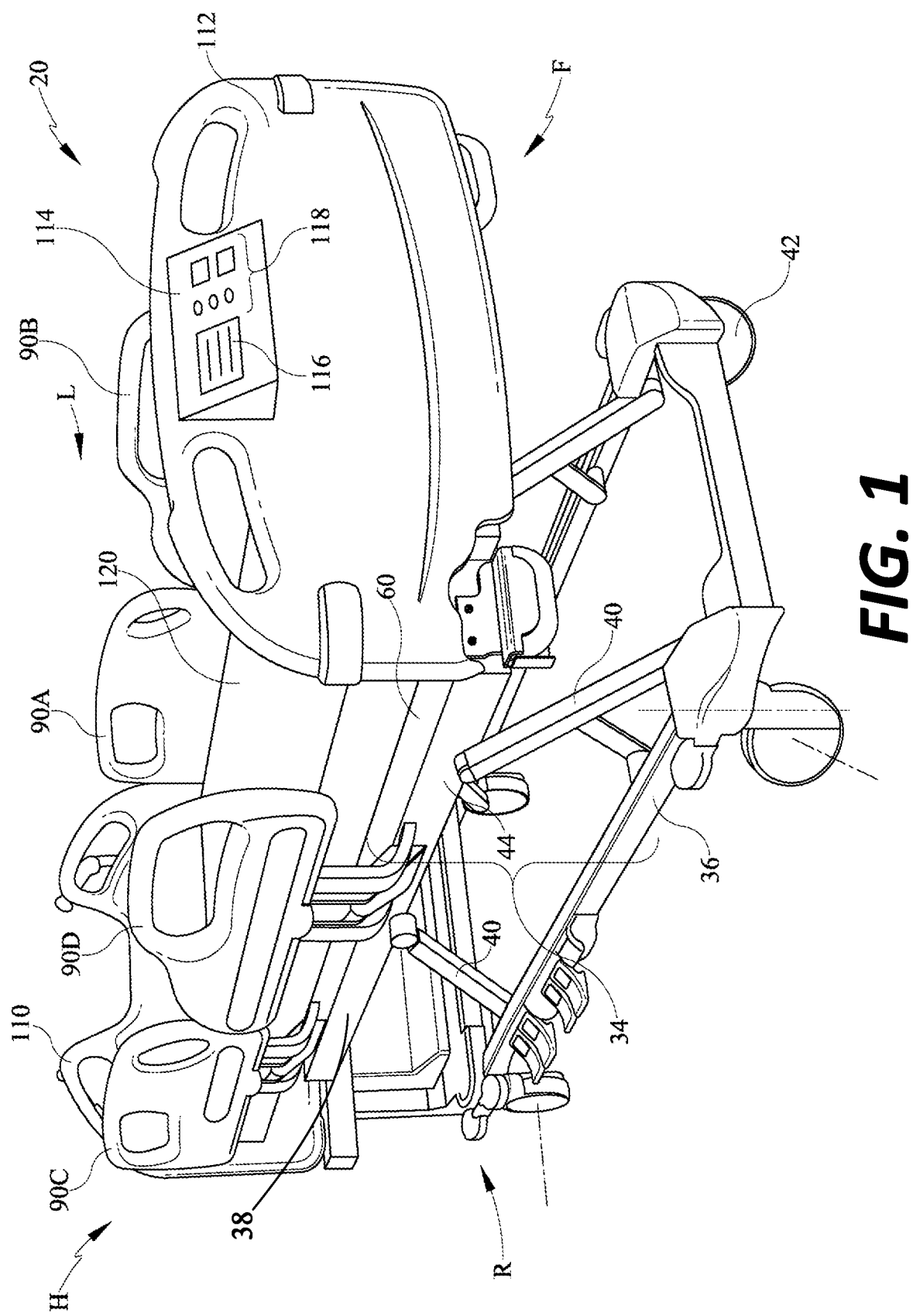
FIG. 1 is a perspective view of a support apparatus.

FIG. 1 is a perspective view of a support apparatus 20. In certain embodiments, the support apparatus 20 is a hospital bed. In alternative embodiments, the support apparatus 20 may be a chair, a recliner, surgical table, or any other support apparatus. The support apparatus 20 may be located in a patient care facility, such as but not limited to a hospital, medical clinic, surgical center, nursing home, skilled nursing facility, or the like, or in a patient's home.

The support apparatus 20 extends longitudinally from a head end H to a foot end F and laterally from a left side L to a right side R, where left and right are taken from the perspective of a supine occupant of the support apparatus 20.

The support apparatus 20 includes a frame 34 that includes a base frame 36 and an elevatable frame 38 that is supported on the base frame 36 by supports 40. The elevatable frame 38 is vertically movable relative to the base frame 36 (see directional arrow V shown in FIG. 2). The frame 34 includes casters 42 extending from the base frame 36 to the floor.

Figure 2:
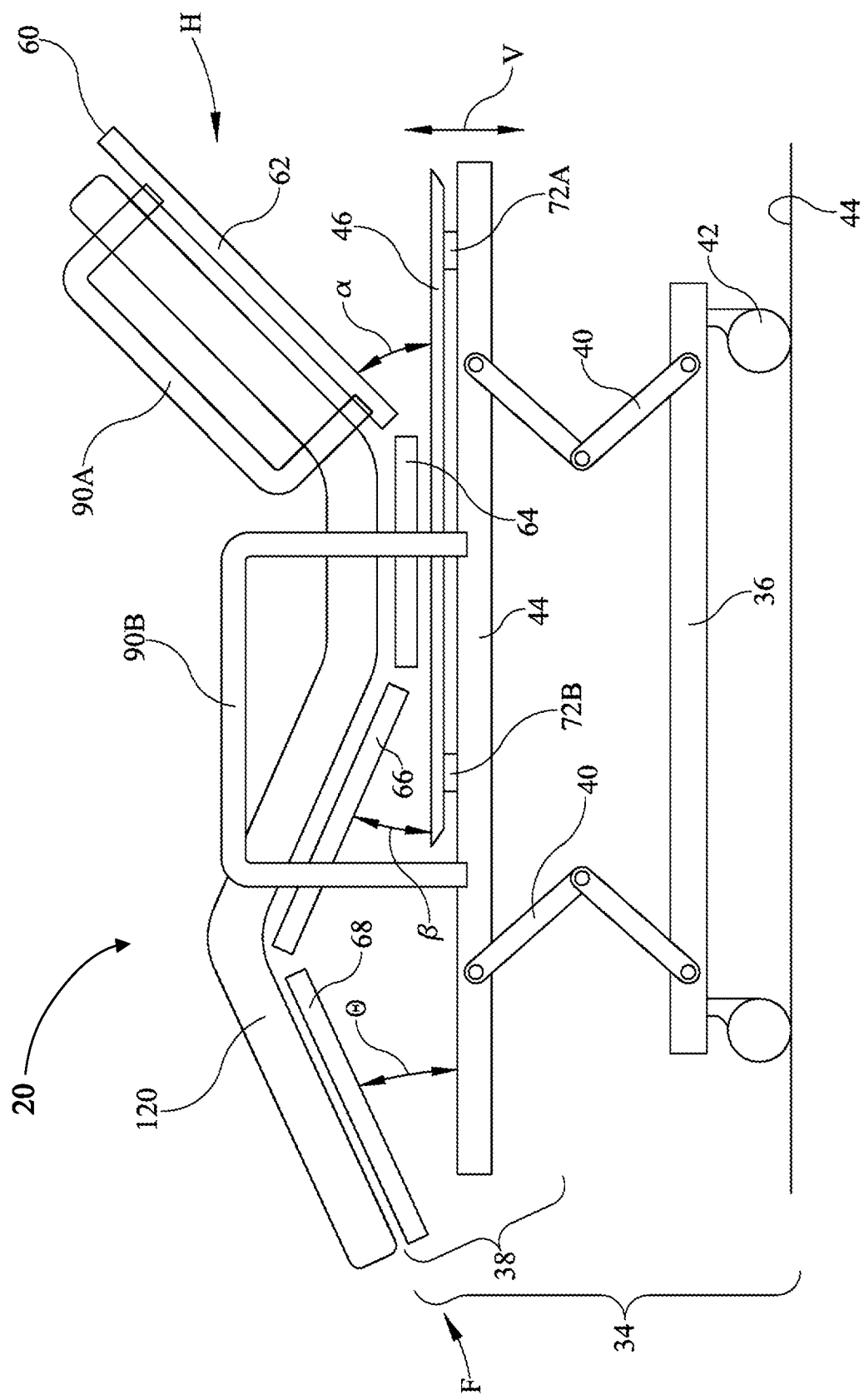
FIG. 2 is a side view of the support apparatus.

FIG. 2 is a side view of the support apparatus 20. The elevatable frame 38 includes a sub-frame 44, a weigh frame 46 and a deck 60. In certain embodiments, the deck 60 is segmented into an upper body section 62 corresponding approximately to a supine occupant's torso, a seat section 64 corresponding approximately to the occupant's buttocks, a thigh section 66 corresponding approximately to the occupant's thighs, and a calf section 68 corresponding approximately to the occupant's calves and feet.

In the example illustrated in the FIG. 2, the upper body section 62, thigh section 66, and calf section 68 are adjusted from a 0 degrees orientation (i.e., parallel to the sub-frame 44) to a nonzero orientation (i.e., not parallel to the sub-frame 44) to change a profile of a mattress 120 that rests on the deck 60. The mattress 120 is flexible such that it conforms to the profile of the deck 60 as the orientation of the deck 60 is adjusted.

Figure 3:
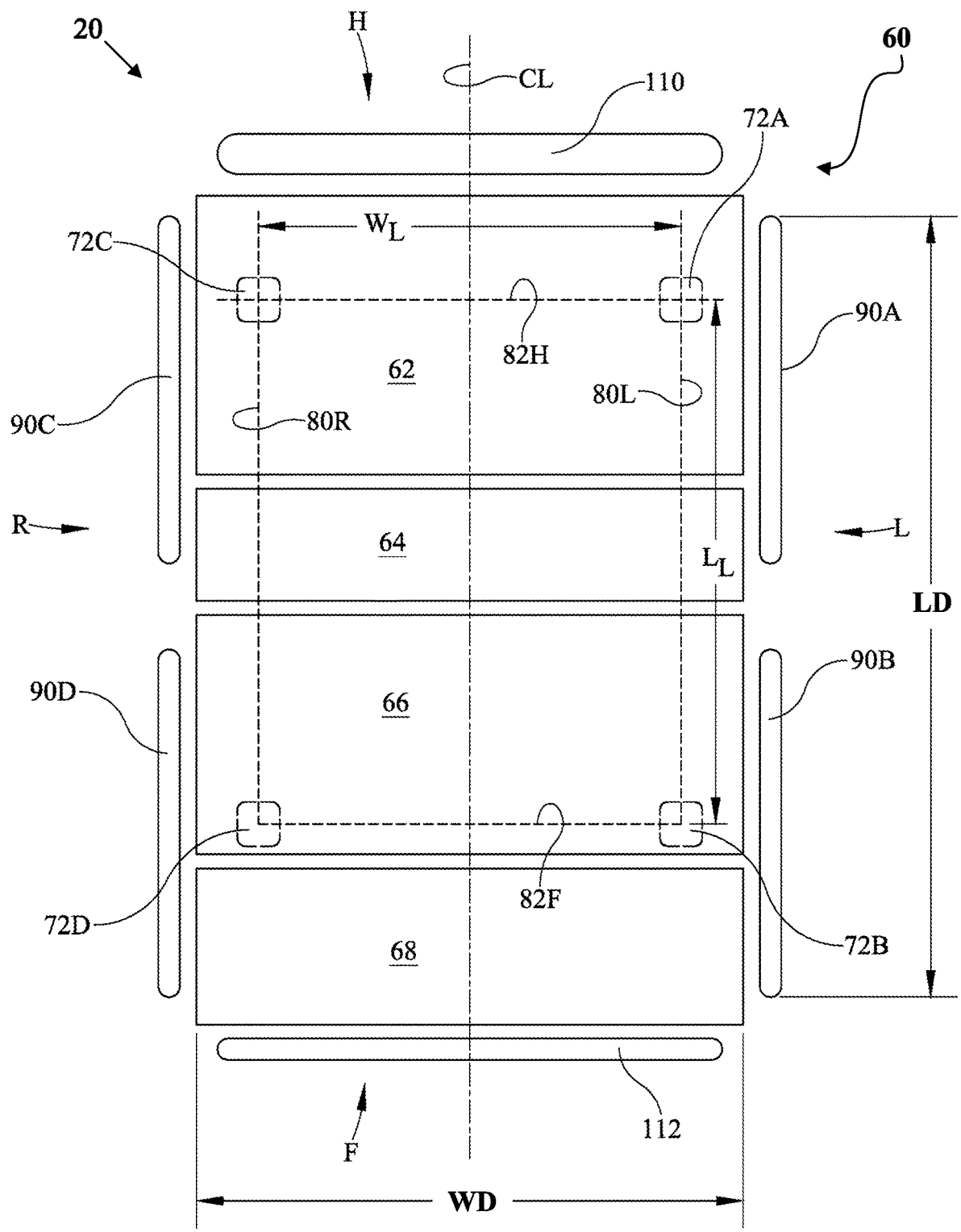
FIG. 3 is a plan view of the support apparatus.

FIG. 3 is a plan view of the support apparatus 20. The deck 60 has a length LD and a width WD. The length LD is designated when each of the sections 62, 64, 66, and 68 is at its minimum angle of orientation with respect to the sub-frame 44 (i.e., when α=β=θ=0).

Referring now to FIGS. 2 and 3, the frame 34 includes one or more force sensors 72A-72D interposed between the weigh frame 46 and sub-frame 44. The force sensors 72 include an upper left force sensor 72A, a lower left force sensor 72B, an upper right force sensor 72C, and a lower right force sensor 72D. The designation "upper" means directed toward the head end H of the support apparatus 20. The designation "lower" means directed toward the foot end F of the support apparatus 20. The "left" and "right" designations are taken from the perspective of a supine occupant of the support apparatus 20.

The force sensors 72A-72D are arranged in a substantially rectangular pattern. Each force sensor 72 outputs a force signal in response to a force exerted on it. Although the force signals are electrical signals, they represent the force exerted on each force sensor 72 and therefore, in the interest of simplicity, are referred to herein as force signals.

The support apparatus 20 includes a left siderail assembly having at least one left siderail mounted on the left side of the frame and a right siderail assembly having at least one right siderail mounted on the right side of the frame. In example embodiment of FIGS. 1-3, the left siderail assembly includes an upper left siderail 90A and a lower left siderail 90B, and the right siderail assembly includes an upper right siderail 90C and a lower right siderail 90D.

The upper siderails 90A, 90C are connected to the upper body section 62 and rotate with the upper body section 62 as that section rotates through angle α (see FIG. 2). The lower siderails 90B, 90D are connected to a portion of the elevatable frame 38 that does not rotate with respect to the sub-frame 44 (see FIG. 2). Accordingly, the lower siderails 90B, 90D are always at a fixed orientation relative to sub-frame 44 as shown in FIG. 2.

Each siderail 90A-90D is positionable at a deployed position at which its upper edge is higher than the top of the mattress 120 and at a stowed position at which its upper edge is lower than the top of the mattress 120. When the deployed position, the siderail prevents the occupant from exiting the support apparatus 20. When in the stowed position, the siderail allows the occupant to enter and exit the support apparatus 20. In some embodiments, the siderails 90A-90D are also positionable at intermediate positions that are not as high as the deployed position nor as low as the stowed position. In the example embodiment illustrated in FIG. 1, all four siderails 90A-90D are in the deployed position.

The positions of the siderails 90A-90D, taken collectively, define a siderail configuration. Certain siderail configurations, such as one in which all four siderails are deployed, may be designated as exit-deterring configurations. Other configurations, such as one in which all four siderails are stowed, may be designated as exit accommodating configurations. Other combinations of deployed positions, stowed positions and intermediate positions (if intermediate positions are available) are possible for the siderails 90A-90D.

As shown in FIGS. 1 and 3, the support apparatus 20 includes a headboard 110 and a footboard 112. In certain embodiments, the footboard 112 is removable from the foot end F of the frame 34 in order to accommodate occupant egress from the foot end F. For example, in certain embodiments, the support apparatus 20 can be adjusted so that its profile mimics that of a chair. When the support apparatus 20 is in a chair-like profile, the footboard 112 can be removed to facilitate egress and ingress at the foot end F of the support apparatus 20.

As shown in FIG. 1, the support apparatus 20 can include a user interface 114. The user interface 114 includes a display 116 for displaying information, and user input devices 118 such as buttons, switches or a keyboard for accepting user inputs. In the example embodiment illustrated in FIG. 1, the user interface 114 is positioned on the footboard 112.

Typically, a support apparatus such as a hospital bed, is a non-automatic weighing instrument which means that before a new patient enters a bed, a caregiver must zero the bed in order to properly weigh the patient. Zeroing the bed requires the caregiver to access a bed scale feature on the bed to indicate that a new patient will enter the bed. This step can easily be overlooked by the caregiver, such that weight-based bed exit alarm systems are susceptible to human error. This is because bed exit alarms are traditionally based around minimum weight thresholds rather than evaluating trends in the patient data collected by the bed. Therefore, proper bed exit functionality is typically reliant on proper scale zeroing.

As will be described in more detail, the support apparatus 20 utilizes an exit prediction system 130 that uses raw A/D counts prior to their conversion into an overall patient weight. Advantageously, this eliminates the need for a caregiver to zero the support apparatus 20 which can reduce human errors associated with bed exit predictions.

Figure 4:
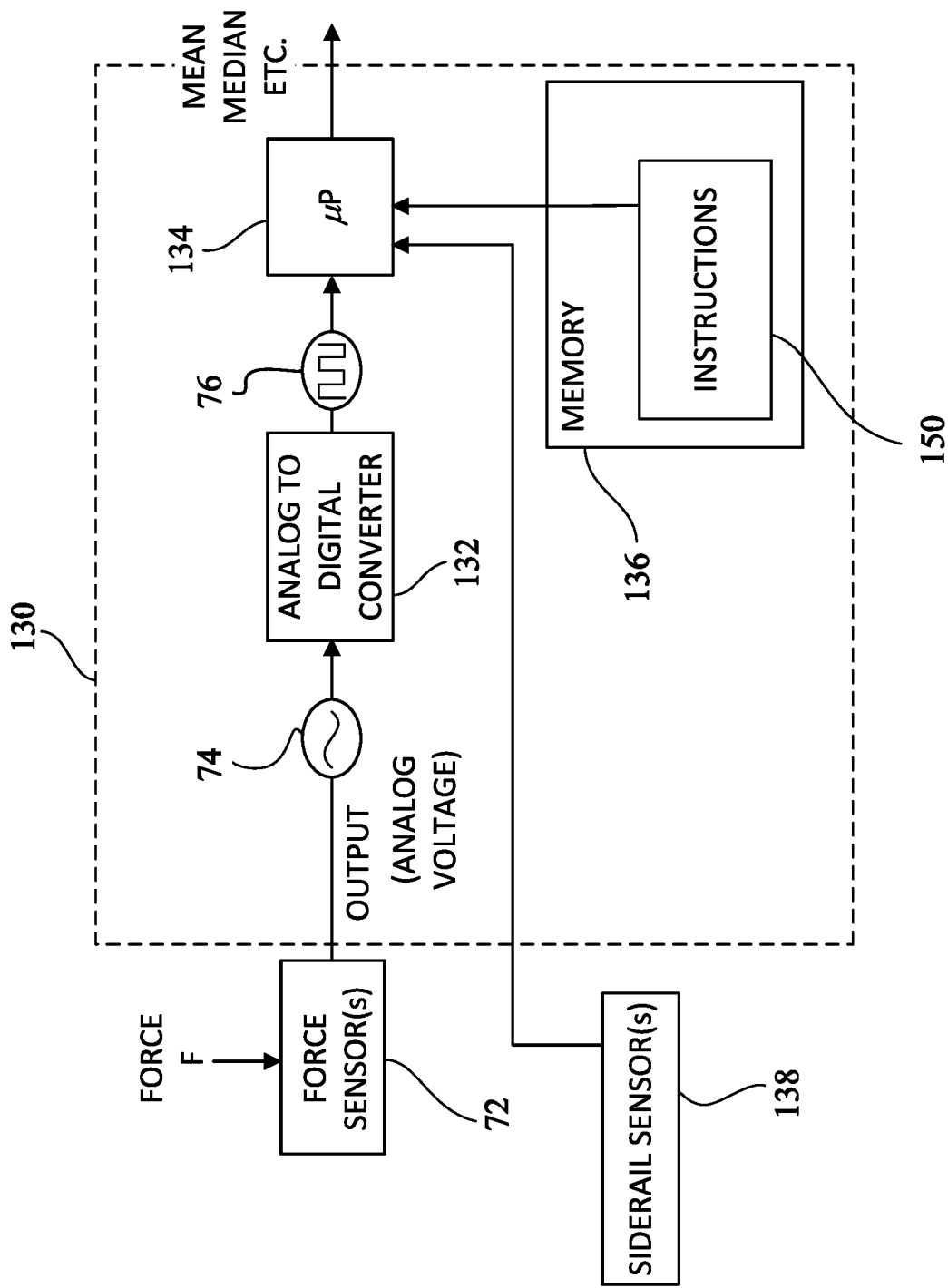
FIG. 4 schematically illustrates an exit prediction system for the support apparatus.

FIG. 4 schematically illustrates an exit prediction system 130 for the support apparatus 20. The exit prediction system 130 includes an analog-to-digital (A/D) converter 132, a processing unit 134, and a system memory 136 in communication with the processing unit 134.

The A/D converter 132 receives analog signals 74 from each force sensor 72, and converts the analog signals 74 into digital signals 76. The analog signal 74 from each force sensor 72 is a voltage or current that corresponds to a force F applied to the force sensor 72. Accordingly, the analog signal 74 from each force sensor 72 varies as the force F applied to the force sensor 72 varies. The digital signal 76 is a discrete number that represents the magnitude of the analog voltage or current. As used herein, the digital signal 76 is an A/D count.

The system memory 136 contains machine-readable instructions 150 executable by the processing unit 134. The machine-readable instructions 150 include algorithms, that when executed by the processing unit 134, use detected changes (Δ) in the A/D counts 76 as inputs to determine movement trends while an occupant is positioned on the support apparatus 20. The detected changes (Δ) in the A/D counts 76 are received from each force sensor 72 individually.

The algorithms do not require a calculation of the weight or center of gravity of the occupant to detect movement trends of the occupant. Advantageously, this means that the force sensors 72 do not need to be zeroed each time a new occupant is positioned on the support apparatus 20. Instead, the one or more algorithms use the detected changes (Δ) in the A/D counts 76 to detect movement trends. By using the detected changes (Δ) in the A/D counts 76 instead of detected shifts in the weight or center of gravity of the occupant, the accuracy of the exit predictions by the exit prediction system 130 can be improved. Also, the force sensors 72 do not need to be re-calibrated for each new occupant of the support apparatus 20.

As further shown in FIG. 4, one or more siderail sensors 138 detect the position of the siderails 90A-90D. For example, each siderail 90A-90D can be equipped with a siderail sensor 138 that detects whether the siderail 90A-

90D is in the deployed, stowed, or intermediate position. In certain embodiments, a siderail sensor 138 can also be used to detect whether the footboard 112 is attached or removed from the foot end F of the frame 34.

In certain embodiments, the algorithms stored in the system memory 136 combine the movement trends derived from the detected changes (Δ) in the A/D counts 76 with additional inputs, such as the position of the siderails 90A-90D detected by the siderail sensors 138, to generate an exit prediction. For example, an exit prediction that an occupant is likely to exit the support apparatus 20 (i.e., a positive exit prediction) is generated by the exit prediction system 130 when detected changes (Δ) in the A/D counts 76 indicate that the occupant is rolling to the left side L of the support apparatus, and the siderail sensors 138 detect that the upper left siderail 90A and lower left siderail 90B are in the stowed position.

Conversely, an exit prediction that the occupant is not likely to exit the support apparatus 20 (i.e., a negative exit prediction) is generated when the siderail sensors 138 detect that the upper left siderail 90A and lower left siderail 90B are in the deployed position despite detected changes (Δ) in the A/D counts 76 that indicate that the occupant is rolling to the left side L of the support apparatus 20. This is because the siderails 90A, 90B will prevent the occupant from rolling off of the left side L of the support apparatus 20 when in the deployed position.

In alternative embodiments, the algorithms stored in the system memory 136 use movement trends derived from the detected changes (Δ) in the A/D counts 76 to generate an exit prediction without any additional inputs. In such embodiments, the exit prediction system 130 generates an exit prediction based exclusively on movement trends.

Additionally, the detected changes (Δ) in the A/D counts 76 can be used to detect and quantify the restlessness of the occupant while positioned on the support apparatus 20. For example, a greater number of detected changes (Δ) in the A/D counts 76 over a fixed period of time indicates that the occupant is moving more frequently, and is hence more restless, than a lower number of detected changes (Δ) in the A/D counts 76 over the same period of time.

Furthermore, regardless of whether the exit prediction system 130 determines that there is a positive or negative exit prediction, the A/D counts 76 can be used identify and monitor the position of the occupant on the support apparatus 20. As an example, a sitting upright position can be detected by the exit prediction system 130 when the detected changes (Δ) in the A/D counts 76 exhibit a rapid drop in the A/D counts 76 from the force sensors 72A, 72C in the upper body section 62 of the deck 60, and a sudden increase in the A/D counts 76 from the force sensors 72B, 72D in the thigh section 66 of the deck 60. Thus, the position of the occupant is identified as sitting upright when the A/D counts 76 from the force sensors 72B, 72D are greater than the A/D counts 76 from the force sensors 72A, 72C in the upper body section 62.

As another example, the position of the occupant on the right side R of the support apparatus 20 is identified by the exit prediction system 130 when the detected changes (Δ) in the A/D counts 76 exhibit a rapid drop in the A/D counts 76 from the force sensors 72A, 72B on the left side L of the support apparatus 20, and a sudden increase in the A/D counts 76 from the force sensors 72C, 72D on the right side R of the support apparatus 20. Thus, the position of the occupant is identified as being on the right side R of the support apparatus 20 when the A/D counts 76 from the force sensors 72C, 72D on the right side R are greater than the A/D counts 76 from the force sensors 72A, 72B located on the left side L of the support apparatus 20.

Figure 5:
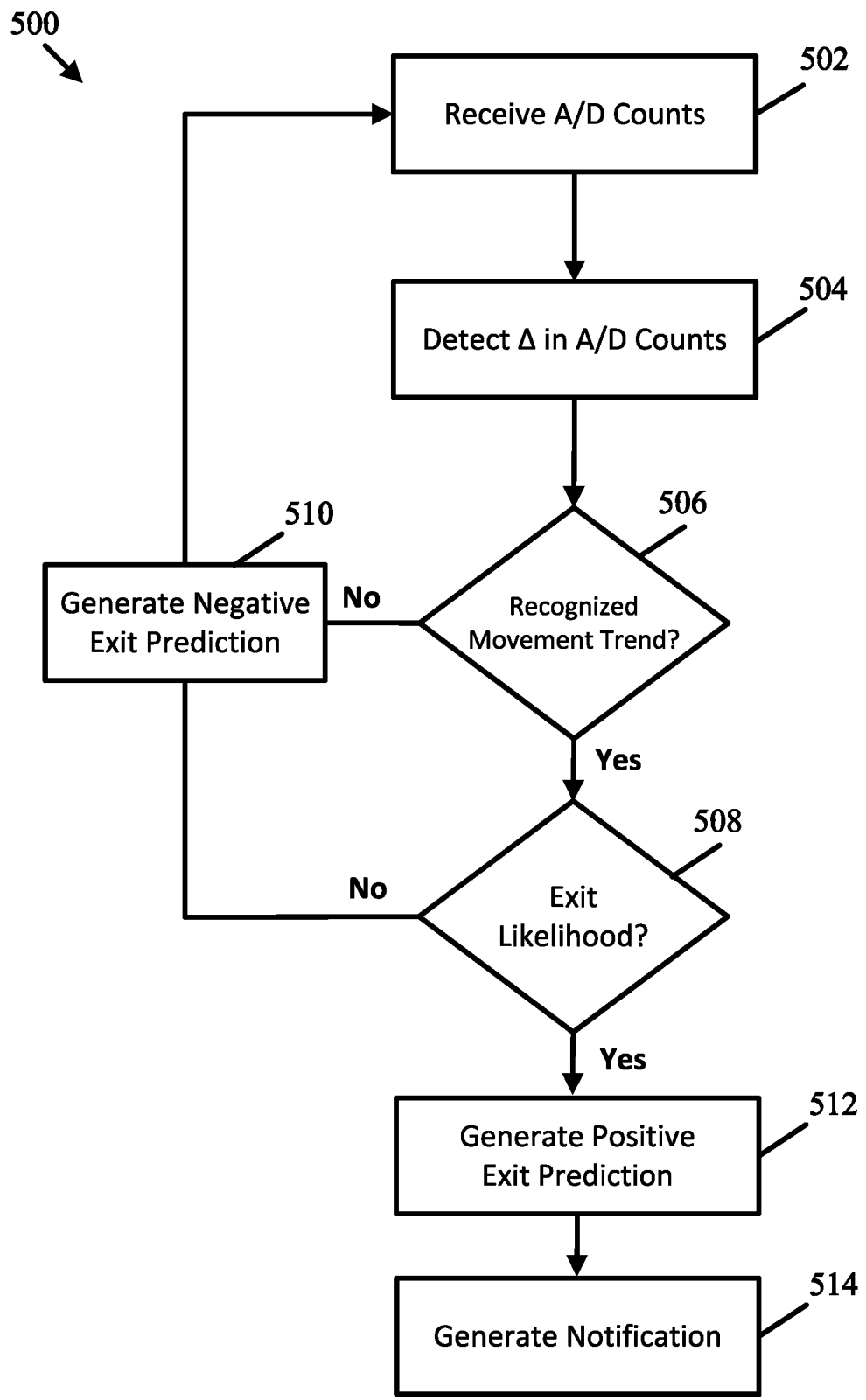
FIG. 5 schematically illustrates a method of generating an exit prediction.

FIG. 5 illustrates a method 500 of predicting an occupant exit from the support apparatus 20. The method 500 includes an operation 502 of receiving the A/D counts 76 from the force sensors 72A-72D. The A/D counts 76 are data inputs representing the voltage or current magnitude of the force sensors 72A-72D. Operation 502 is done without having to zero the force sensors 72A-72D. The A/D counts 76 are received from each force sensor 72 individually, and are not combined to determine the weight or center of gravity of the occupant. Thus, the method 500 does not rely on calculating the weight or center of gravity of the occupant in order to predict an occupant exit from the support apparatus 20.

This is advantageous because errors in predicting occupant exit in some alternative systems are attributable to the failure to zero the force sensors before a new occupant is placed on a support apparatus such as a hospital bed. Zeroing typically means summing the detected weight values before an occupant is positioned on a support apparatus to determine a baseline weight. Any increase from the baseline weight is inferred as the result of the occupant being placed on the support apparatus. However, if the baseline weight is incorrectly zeroed, systems that rely on calculating the weight or center of gravity of an occupant to predict an occupant exit can fail to perform correctly. For example, if the baseline weight is incorrect such that it is established as a negative value, an algorithm that uses occupant weight for determining an occupant exit will not start at the right point such that when an occupant shifts their body to exit the support apparatus, the shift in weight may not reach a threshold level to sound an exit alarm. Thus, by not relying on calculating the weight or center of gravity of an occupant in order to predict an occupant exit, the method 500 can more accurately and consistently predict an occupant exit from the support apparatus 20.

Next, the method 500 includes an operation 504 of detecting changes (Δ) in the A/D counts 76 received from the force sensors 72A-72D. The changes (Δ) are detected without regard to the weight or center of gravity of the occupant of the support apparatus 20. Instead, the changes (Δ) are detected based only on the A/D counts 76 which, as described above, represent the voltage or current magnitude associated with each of the force sensors 72A-72D.

Next, the method 500 includes an operation 506 of determining whether the detected changes (Δ) are indicative of a movement trend. As an example, when an occupant of the support apparatus 20 moves from a supine position to a sitting upright position, the A/D counts 76 from the force sensors 72A, 72C located in the upper body section 62 of the deck 60 (see FIG. 3) will decrease, and the A/D counts 76 from the force sensors 72B, 72D located in the thigh section 66 of the deck 60 will increase. Thus, detected changes (Δ) in the A/D counts 76 from the force sensors 72A-72D can be used to determine a movement trend for an occupant of the support apparatus such as moving from a supine position to a sitting upright position.

As another example, when an occupant of the support apparatus 20 rolls to the left side L while in the support apparatus 20, the A/D counts 76 from the force sensors 72C, 72D located on the right side R of the support apparatus 20 will decrease, and the A/D counts 76 from the force sensors 72A, 72B located on the left side L of the support apparatus 20 will increase. Thus, detected changes (Δ) in the A/D counts 76 from the force sensors 72A-72D can be used to determine a movement trend such as rolling to the left side L of the support apparatus 20.

As another example, when an occupant of the support apparatus 20 rolls to the right side R while in the support apparatus 20, the A/D counts 76 in the force sensors 72A, 72B located on the left side L of the support apparatus 20 will decrease, and the A/D counts 76 in the force sensors 72C, 72D located on the right side R of the support apparatus 20 will increase. Thus, detected changes (Δ) in the A/D counts 76 from the force sensors 72A-72D can be used to determine a movement trend such as rolling to the right side R of the support apparatus 20.

In some embodiments, predefined changes (Δ) in A/D counts associated with movement trends are stored in the system memory 136. In some examples, the movement trends are associated with movements typically performed by occupants in order to exit the support apparatus 20 such as the movements described above including, without limitation, moving from a supine position to a sitting upright position, rolling to the left side L of the support apparatus 20, and rolling to the right side R of the support apparatus 20.

Operation 506 can include comparing the detected changes (Δ) (from operation 504) to the predefined changes (Δ) to determine whether the detected changes (Δ) are indicative of a movement trend. The comparison can be performed by the processing unit 134.

In some instances, one or more thresholds are used to determine whether the detected changes (Δ) sufficiently match the predefined changes (Δ) associated with the movement trends. For example, when the detected changes (Δ) are within a predetermined threshold, operation 506 determines that the detected changes (Δ) are indicative of a movement trend (i.e., "Yes" at operation 506). When the detected changes (Δ) are outside a predetermined threshold, operation 506 determines that the detected changes (Δ) are not indicative of a movement trend (i.e., "No" at operation 506). In some example embodiments, machine learning can be used to recognize trends in the detected changes (Δ) from operation 504 to determine whether the detected changes (Δ) are indicative of a movement trend at operation 506.

Advantageously, by using the changes (Δ) in the A/D counts 76 instead of a calculated weight or center of gravity for the occupant of the support apparatus 20, a technical effect is produced by reducing the computational complexity of the method 500 which can reduce the strain on the processing unit 134, and can improve computer performance. Also, this can improve the accuracy and reliability of the exit prediction.

When a change (Δ) in the A/D counts 76 is not detected, or when a change (Δ) in the A/D counts 76 is not indicative of a movement trend (i.e., "No" at operation 506), the method 500 proceeds to operation 510 to generate a negative exit prediction which means that an occupant of the support apparatus 20 is not likely to exit. When a negative exit prediction is generated, no notifications or alarms are generated. Instead, the method 500 returns to operation 502 to continue to receive the A/D counts 76 from the force sensors 72A-72D.

When changes (Δ) are indicative of a movement trend (i.e., "Yes" at operation 506), the method 500 proceeds to an operation 508 of determining whether the movement trend is indicative of a likelihood for the occupant to exit the support apparatus 20. Operation 508 can includes applying control rules to the movement trend to determine an exit prediction. As used herein, an exit prediction is a likelihood for an occupant to exit the support apparatus 20. In some examples, the control rules include Shewhart control logic. Multiple control rules may be applied to increase the sensitivity of the exit prediction, while keeping false positives at a minimum.

An example of a control rule is identifying a patient as sitting up by detecting a change (Δ) in the A/D counts of greater than 25% shifting from the head end H to the foot end F of the support apparatus 20. Another example of a control rule is identifying a patient as moving towards the edge of the bed by detecting a change (Δ) in the A/D counts of greater than 25% shifting from the right side R to the left side L of the support apparatus 20. Additional examples of control rules are possible. Advantageously, the control rules based on detected changes (Δ) in the A/D counts can increase the sensitivity of the exit prediction system 130. For example, the exit prediction system 130 can activate an alarm within three seconds of a bed exit event in order to give caregivers time to react and improve on bed exit functions currently in place.

When it is determined that the occupant is not likely to exit the support apparatus (i.e., "No" at operation 508), the method 500 proceeds to operation 510 to generate a negative exit prediction. Thereafter, the method 500 returns to operation 502. Advantageously, by determining whether the detected changes (Δ) in the A/D counts are indicative of a movement trend (operation 506), and then determining whether the movement trend is indicative of an occupant exit (operation 508), false alarms can be reduced.

When it is determined that the occupant is likely to exit the support apparatus (i.e., "Yes" at operation 508), the method 500 proceeds to operation 512 to generate a positive exit prediction which means that the occupant is likely to exit the support apparatus 20. While operations 510 and 512 suggest a binary choice between generating a positive or negative exit prediction, it is contemplated that additional exit predictions are possible such as a range of exit predictions that include intermediate likelihoods (e.g., between highly likely and highly unlikely) to provide further granularity in predicting an occupant exit from the support apparatus 20.

In response to generating a positive exit prediction at operation 512, the method 500 can further include an operation 514 of generating one or more types of notifications. Example notifications include sounding a local alarm on the support apparatus 20, sounding an alarm at a nurses' station, and/or sending an alert message directly to one or more caregivers. Examples of local alarms on the support apparatus 20 can include illuminating a warning light on the display 116 of the support apparatus 20 (see FIG. 1), or generating an audible alarm warning the occupant or caregiver of the danger of exiting the support apparatus without assistance.

Figure 6:
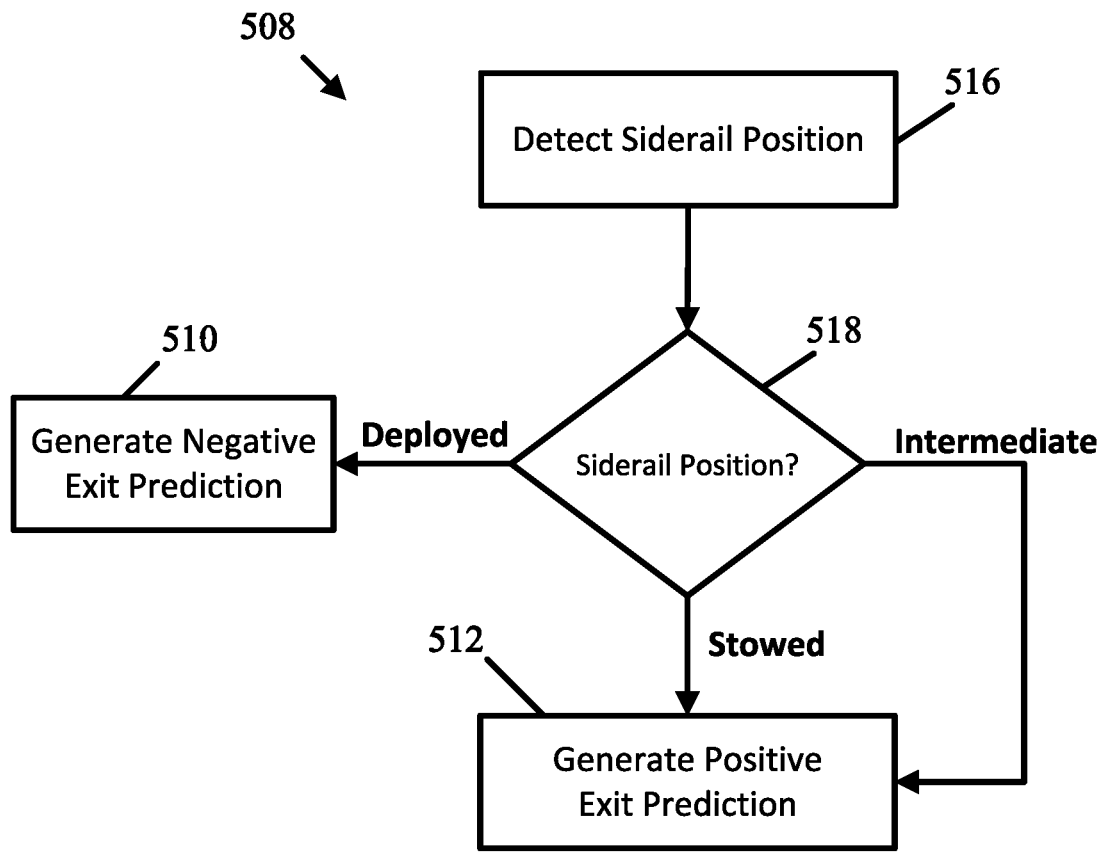
FIG. 6 schematically illustrates an operation within the method of FIG. 5.

FIG. 6 schematically illustrates an example embodiment of operation 508 from the method 500. As described above, operation 508 determines whether the occupant is likely to exit the support apparatus 20. In the example embodiment of FIG. 6, operation 508 includes a sub-operation 516 of detecting the position of the siderails 90A-90D based on the signals received from the one or more siderail sensors 138. As described above, each siderail 90A-90D is positionable between deployed, intermediate, and stowed positions.

In some embodiments, sub-operation 516 can further include receiving signals from the one or more siderail sensors 138 to detect whether the footboard 112 is attached or removed from the foot end F of the frame 34. When the footboard 112 is removed from the frame 34, the occupant can exit the support apparatus 20 from the foot end F of the frame.

Next, operation 508 includes determining whether the movement trend (determined from operation 506) is directed in a direction toward a siderail 90A-90D that is in a deployed position, intermediate position, or stowed position. For example, the detected changes (Δ) in the A/D counts 76 can trend toward the left side L of the support apparatus 20 where the siderails 90A, 90B of the left siderail assembly are located, or can trend toward the right side R of the support apparatus 20 where the siderails 90C, 90D of the right siderail assembly are located. Additionally, the detected changes (Δ) in the A/D counts 76 can trend toward the foot end F of the support apparatus 20 where the footboard 112 is located.

When the movement trend is directed towards a siderail 90A-90D that is in the deployed position (i.e., "Deployed" at operation 518), the siderail will prevent the occupant from exiting the support apparatus 20 such that a negative exit prediction is generated at operation 510. As described above, when a negative exit prediction is generated, no notifications or alarms are generated. Instead, the method 500 returns to operation 502 to continue to receive and monitor the changes (Δ) in the A/D counts 76.

When the movement trend is directed towards a siderail 90A-90D that is in the stowed position (i.e., "Stowed" at operation 518), the siderail will not prevent the occupant from exiting the support apparatus 20 such that a positive exit prediction is generated at operation 512. In some embodiments, when the movement trend is directed towards the foot end F of the support apparatus 20, and the footboard 112 is detected as being removed from the frame 34, a positive exit prediction is generated at operation 512 because the footboard 112 will not prevent the occupant from exiting the support apparatus 20.

When the movement trend is directed towards a siderail 90A-90D that is in the intermediate position (i.e., "Intermediate" at operation 518), the method 500 proceeds to generate a positive exit prediction at operation 512 because the siderails 90A-90D when in the intermediate position do not entirely prevent the occupant from exiting the support apparatus 20.

As described above, in response to generating a positive exit prediction at operation 512, the method 500 can include an operation 514 (see FIG. 5) of generating notifications such as sounding a local alarm on the support apparatus 20, sounding an alarm at a nurses' station, and/or sending an alert message directly to one or more caregivers.

In some embodiments, the notifications that are generated when the movement trend is directed towards a siderail 90A-90D in the intermediate position are less severe than the notifications generated when the movement trend is directed towards a siderail 90A-90D in the stowed position. For example, when the movement trend is directed toward a siderail 90A-90D in the intermediate position, the method 500 can generate a moderate notification that identifies a potential exit from the support apparatus 20. By generating a moderate notification, the method 500 can reduce alarm fatigue.

Figure 7:
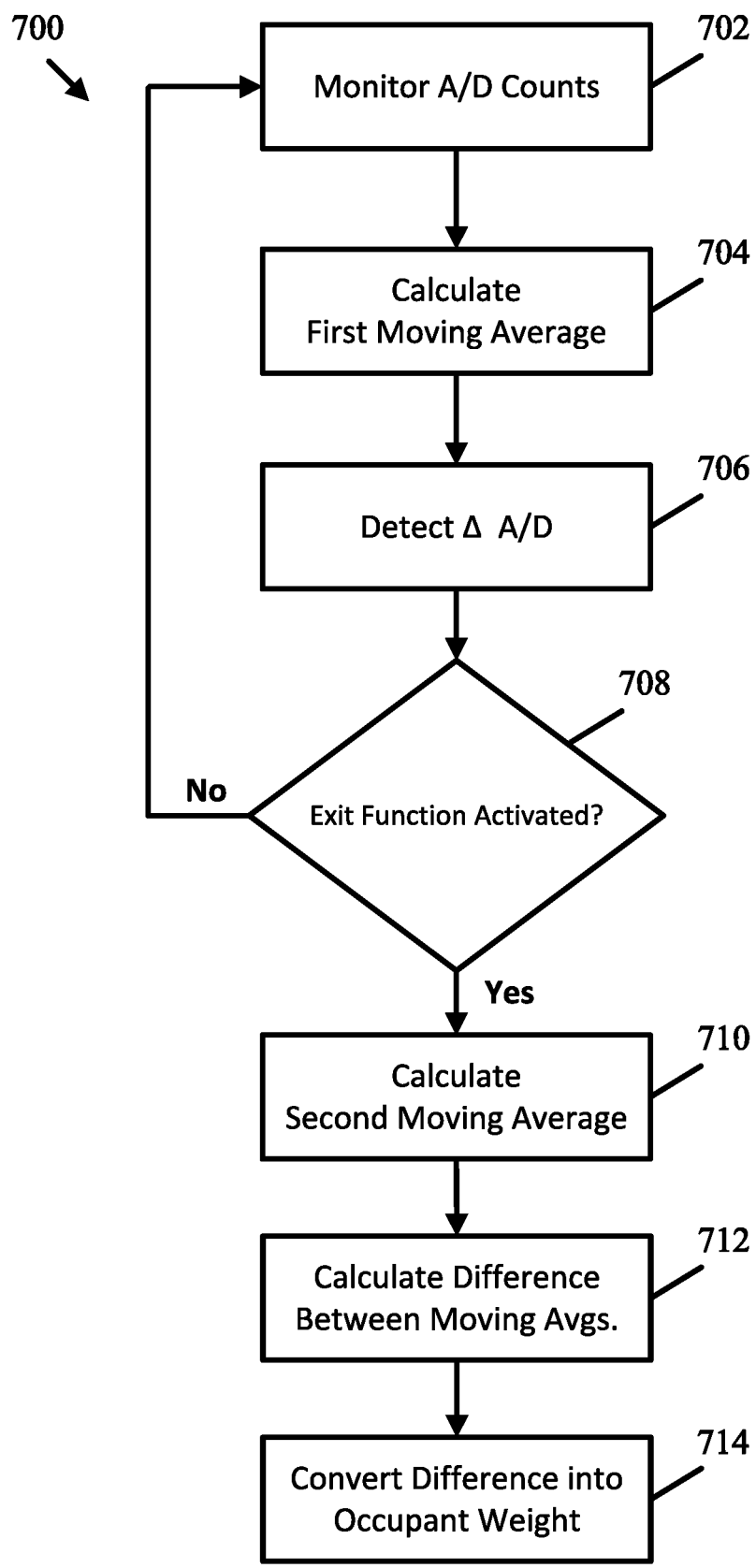
FIG. 7 schematically illustrates a method of estimating occupant weight.

FIG. 7 schematically illustrates a method 700 of automatically estimating an occupant weight. The method 700 does not require a caregiver to establish a baseline weight before the occupant is positioned on the support apparatus 20 such that the caregiver does not have to zero the force sensors 72A-72C each time a new occupant is positioned on the support apparatus 20. Instead, a new baseline weight is automatically established each time an exit routine is activated by the caregiver. Exit alarms are generated only after an exit routine is activated which can advantageously reduce false alarms, and mitigate alarm fatigue.

The method 700 includes an operation 702 of receiving the A/D counts 76 from the force sensors 72A-72D without zeroing the force sensors. The A/D counts 76 are data inputs that represent the voltage or current magnitude of the force sensors 72A-72D. The A/D counts 76 are received from each force sensor 72 individually.

Next, the method 700 includes an operation 704 of calculating a first moving average of the A/D counts 76 received from each force sensor 72A-72D over a predetermined period of time. In some instances, the predetermined period of time is about 15 to 30 seconds. The first moving average is representative of a baseline weight of the support apparatus 20 which is a weight before an occupant is positioned on the support apparatus 20.

Next, the method 700 includes an operation 706 of detecting a change (Δ) in the A/D counts from at least one of the force sensors 72A-72D. For example, a change (Δ) in the A/D counts is detected when an occupant sits or lays down on the support apparatus 20 such that a significant increase in force is applied to the force sensors 72A-72D. During operation 706, the first moving average is stored before the change (Δ) in the A/D counts is detected.

Next, the method 700 includes an operation 708 of determining whether an exit function is activated. An exit function can be activated by using the user input devices 118 on the user interface 114 of the support apparatus 20 (see FIG. 1). The exit function also activates the implementation of the method 500 on the support apparatus 20. In some embodiments, the exit function can be activated within a predetermined period of time (e.g., 30 to 60 seconds) after operation 706, such that the exit function does not need to be activated before operation 706.

When the exit function is not activated (i.e., "No" at operation 708), the method 700 classifies the detected change (Δ) in the A/D counts as a transient condition, and returns to operation 704 to resume calculating the first moving average of the A/D counts 76 received from each force sensor 72A-72D. When the exit function is activated (i.e., "Yes" at operation 708), the first moving average from operation 704 is stored while the bed exit function remains activated.

Upon activation of the exit function, the method 700 proceeds to operation 710 of calculating a second moving average of the A/D counts 76 received from each force sensor 72A-72D over a predetermined period of time. The predetermined period of time for calculating the second moving average is the same as the predetermined period of time used for calculating the first moving average. In certain embodiments, the predetermined period of time for calculating the second moving average is about 15 to 30 seconds. The second moving average is representative of a loaded weight value (i.e., the baseline weight plus the occupant weight).

The method 700 includes an operation 712 of calculating a difference between the first and second moving averages of the A/D counts 76, and followed by an operation 714 of converting the calculated difference into an occupant weight. The calculated difference can be converted into kilograms (kgs) or pounds (lbs) by using a looking up table stored in the system memory 136. The calculated difference in the first and second moving averages is converted into the occupant weight instead of converting the first and second moving averages into converted weights, and then subtracting the converted weights from one another. Advantageously, this can provide a technical effect by reducing the computational complexity of the method 700, and thereby reduce the strain on the processing unit 134 and improve computer performance. Additionally, this can improve the accuracy and reliability of the occupant weight determination.

In certain embodiments, when the exit function is deactivated, the method 700 determines a new baseline value when there is a significant drop in the output from the force sensors 72A-72D. A significant drop in the output from the force sensors 72A-72D is indicative that the occupant has exited the support apparatus 20, such that the apparatus is empty.

Figure 8:
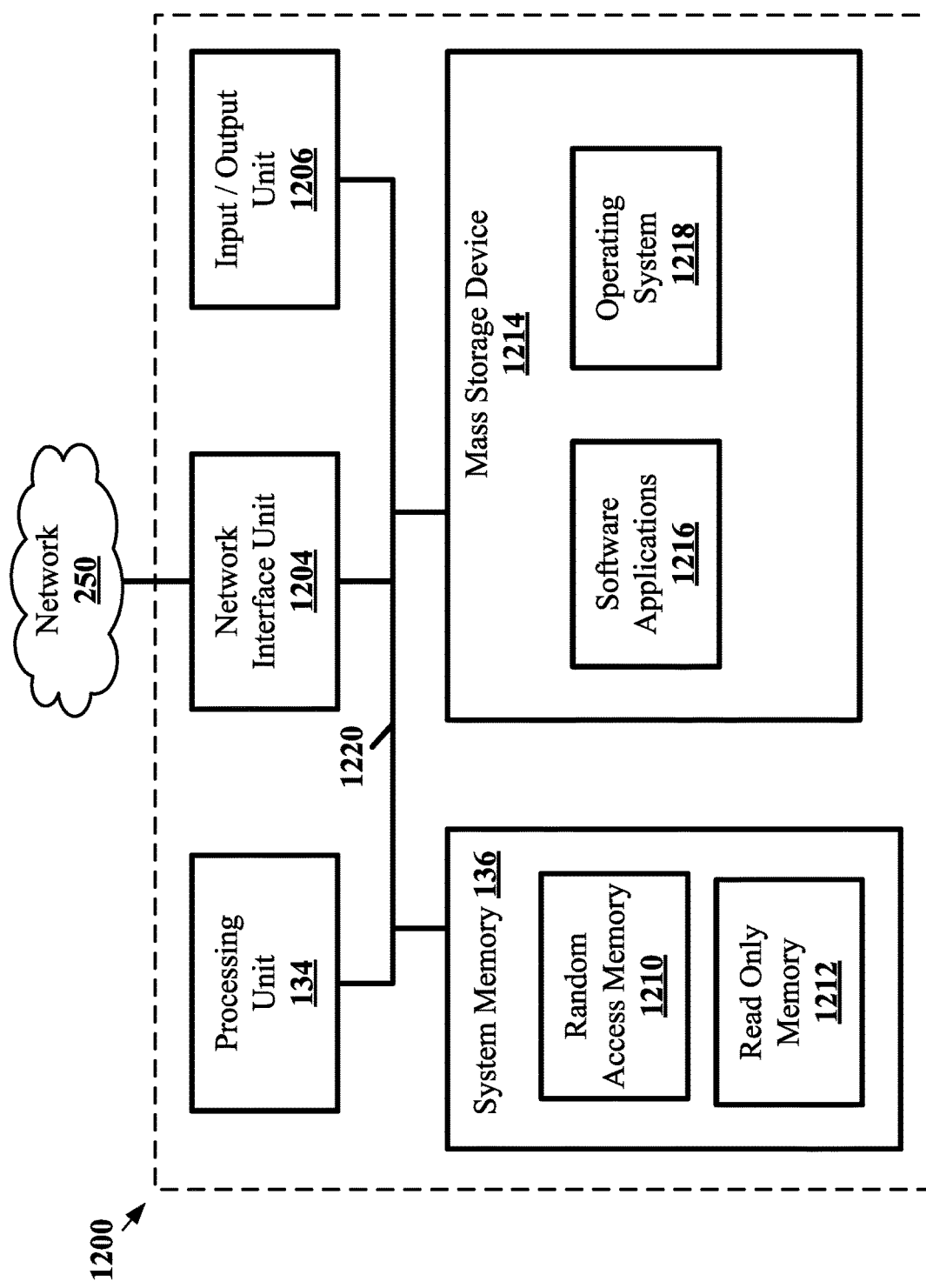
FIG. 8 schematically illustrates an example of a computing device of the exit prediction system that can be used to implement aspects of the present disclosure.

FIG. 8 schematically illustrates an example of a computing device 1200 of the exit prediction system 130 that can be used to implement aspects of the present disclosure, including the methods described herein. The computing device 1200 includes the processing unit 134 and the system memory 136 (see also FIG. 4), and further includes a system bus 1220 that couples the system memory 136 to the processing unit 134. The processing unit 134 is an example of a processing device. For example, the processing unit 134 can be a central processing unit (CPU).

The system memory 136 includes a random-access memory ("RAM") 1210 and a read-only memory ("ROM") 1212. Input/output logic containing routines to help transfer information between elements of the computing device 1200 can be stored in the ROM 1212.

Additionally, the computing device 1200 can further include a mass storage device 1214 that is able to store software instructions and data. The mass storage device 1214 is connected to the processing unit 134 through the system bus 1220. The mass storage device 1214 and its associated computer-readable data storage media provide non-volatile, non-transitory storage for the computing device 1200.

Although the description of computer-readable data storage media contained herein refers to a mass storage device, it should be appreciated by those skilled in the art that computer-readable data storage media can be any available non-transitory, physical device or article of manufacture from which the device can read data and/or instructions. The mass storage device 1214 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The computing device 1200 may operate in a networked environment using logical connections to remote network devices through the network 250, such as a local network, the Internet, or another type of network. The device connects to the network 250 through a network interface unit 1204 connected to the system bus 1220. The network interface unit 1204 may also be utilized to connect to other types of networks and remote computing systems.

The computing device 1200 can also include an input/output controller 1206 for receiving and processing input from a number of input devices. Similarly, the input/output controller 1206 may provide output to a number of output devices.

The mass storage device 1214 and the RAM 1210 can store software instructions and data. The software instructions can include an operating system 1218 suitable for controlling the operation of the computing device 1200. The mass storage device 1214 and/or the RAM 1210 also store software applications 1216, that when executed by the processing unit 134, cause the computing device 1200 to provide the functionality and perform the methods described herein.

The various embodiments described above are provided by way of illustration only and should not be construed to be limiting in any way. Various modifications can be made to the embodiments described above without departing from the true spirit and scope of the disclosure.

What is claimed is:

1. An exit prediction system comprising:
    a bed including:
        a frame;
        one or more force sensors positioned on the frame; and
        a computing device included on the bed, the computing device including:
            a processing unit; and
            a memory in communication with the processing unit; the memory storing machine-readable instructions that, when executed by the processing unit, cause the processing unit to:
                receive data inputs from the one or more force sensors, the data inputs being received without zeroing the one or more force sensors, wherein the data inputs are analog-to-digital (A/D) counts;
                detect changes in the data inputs from the one or more force sensors, wherein the detected changes in the data inputs are detected changes in the A/D counts received from each of the force sensors individually;
                store predefined changes in A/D counts associated with movement trends, wherein the movement trends are associated with movements performed by occupants in order to exit the bed;
                determine whether the detected changes indicate a movement trend by comparing the detected changes to the predefined changes to determine whether the detected changes are indicative of the movement trend;
                determine an exit prediction based at least partially on the movement trend, the exit prediction being determined without combining the data inputs from the one or more force sensors to determine a weight of an occupant of the bed; and
                generate a notification based on the exit prediction, wherein the notification is generated on the bed.

2. The system of claim 1, wherein the A/D counts are derived from analog signals received from the one or more force sensors.

3. The system of claim 2, wherein the analog signals are voltages that correspond to forces applied to the one or more force sensors.

4. The system of claim 3, further comprising an analog-to-digital converter that converts the analog signals from the one or more force sensors into the A/D counts.

5. The system of claim 1, wherein control rules are applied to the movement trend to determine the exit prediction, and the control rules include Shewhart control logic.

6. The system of claim 1, further comprising one or more siderail sensors that detect a position of one or more siderails of the bed, and wherein the exit prediction is at least partially based on the movement trend and the position of the one or more siderails.

7. The system of claim 6, wherein the one or more siderail sensors detect whether a footboard is attached to the bed, and wherein the exit prediction is at least partially based on the movement trend and whether the footboard is attached to the bed.

8. A method of predicting an occupant exit from a support apparatus, the method comprising:
receiving data inputs detected from one or more force sensors positioned on a frame of the support apparatus, wherein the data inputs are analog-to-digital (A/D) counts representing voltage or current magnitudes of the one or more force sensors, and the data inputs are received without zeroing the one or more force sensors;
detecting changes in the data inputs from the one or more force sensors without combining the data inputs to determine a weight of an occupant of the support apparatus, the detected changes in the data inputs are detected changes in the A/D counts received from each of the force sensors individually;
storing predefined changes in A/D counts associated with movement trends, wherein the movement trends are associated with movements performed by occupants in order to exit the support apparatus;
determining whether the detected changes indicate a movement trend by comparing the detected changes to the predefined changes to determine whether the detected changes are indicative of the movement trend;
determining an exit prediction based at least partially on the movement trend, the exit prediction indicating a likelihood for the occupant exit from the support apparatus; and
generating a notification based on the exit prediction, wherein the notification is generated on the support apparatus.

9. The method of claim 8, wherein the movement trend includes moving from a supine position to a sitting upright position, rolling from a right side to a left side, and rolling from the left side to the right side while being positioned on the support apparatus.

10. The method of claim 8, further comprising:
using machine learning to recognize trends in the detected changes to determine whether the detected changes indicate the movement trend.

11. The method of claim 8, further comprising:
applying control rules to determine the exit prediction from the movement trend, wherein the control rules include Shewhart control logic.

12. The method of claim 8, further comprising:
detecting a position of one or more siderails of the support apparatus, the one or more siderails being positionable between deployed, intermediate, and stowed positions;
determining that the movement trend is directed toward a siderail of the one or more siderails that is in the stowed or intermediate position; and
generating an exit prediction that the occupant is likely to exit the support apparatus.

13. The method of claim 8, further comprising:
detecting that a footboard has been removed from the support apparatus;
determining that the movement trend is directed toward a foot end of the support apparatus; and
generating an exit prediction that the occupant is likely to exit the support apparatus.

* * * * *